United States Patent [19]
Hupf

[11] Patent Number: 5,698,769
[45] Date of Patent: Dec. 16, 1997

[54] METHOD AND APPARATUS FOR FINISH SURFACE TESTING

[75] Inventor: Charles J. Hupf, Cascade, Wis.

[73] Assignee: Regal Ware, Inc., Kewaskum, Wis.

[21] Appl. No.: 649,786

[22] Filed: May 17, 1996

[51] Int. Cl.⁶ ............................................. G01N 3/56
[52] U.S. Cl. ................................... 73/7; 73/150 R
[58] Field of Search ........................ 73/7, 78, 81, 8, 73/866, 150 R

[56] References Cited

U.S. PATENT DOCUMENTS

| | | | |
|---|---|---|---|
| 2,114,029 | 4/1938 | Pery | 73/7 |
| 2,962,890 | 12/1960 | Borrino | 73/7 |
| 3,664,888 | 5/1972 | Oga et al. | 148/272 |
| 3,932,941 | 1/1976 | Ormsby | 73/7 |
| 3,961,521 | 6/1976 | Bailey et al. | 73/7 |
| 4,196,611 | 4/1980 | Suga | 73/7 |
| 4,285,728 | 8/1981 | Babcock et al. | 501/7 |
| 4,751,016 | 6/1988 | Tse et al. | 252/174.25 |
| 4,864,852 | 9/1989 | Boone | 73/7 |
| 4,914,146 | 4/1990 | Honda et al. | 524/441 |
| 4,936,135 | 6/1990 | Annis et al. | 73/7 |
| 5,106,682 | 4/1992 | Matsushita et al. | 428/324 |
| 5,326,728 | 7/1994 | Boury et al. | 501/17 |
| 5,375,451 | 12/1994 | Sandstrom | 73/7 |
| 5,531,095 | 7/1996 | Hupf | 73/7 |

FOREIGN PATENT DOCUMENTS

173475   9/1965   U.S.S.R.

*Primary Examiner*—Thomas P. Noland
*Attorney, Agent, or Firm*—Wheeler Kromholz & Manion

[57] ABSTRACT

An apparatus and method for testing the mechanical durability of a test surface finish of an object, such as a cooking vessel. The apparatus consists principally of a sliding support fixture operated by a gearmotor with an eccentric drive providing alternative forward and rearward movement to the fixture, scrapers for contacting the surface finish in a predetermined path, and individually operated coil springs for applying constant pressure to the scrapers during the test scraping cycle. A cam and lever combination is also supplied to raise the scrapers above the surface finish as they are returned to initial start position during cyclical test operation.

8 Claims, 7 Drawing Sheets

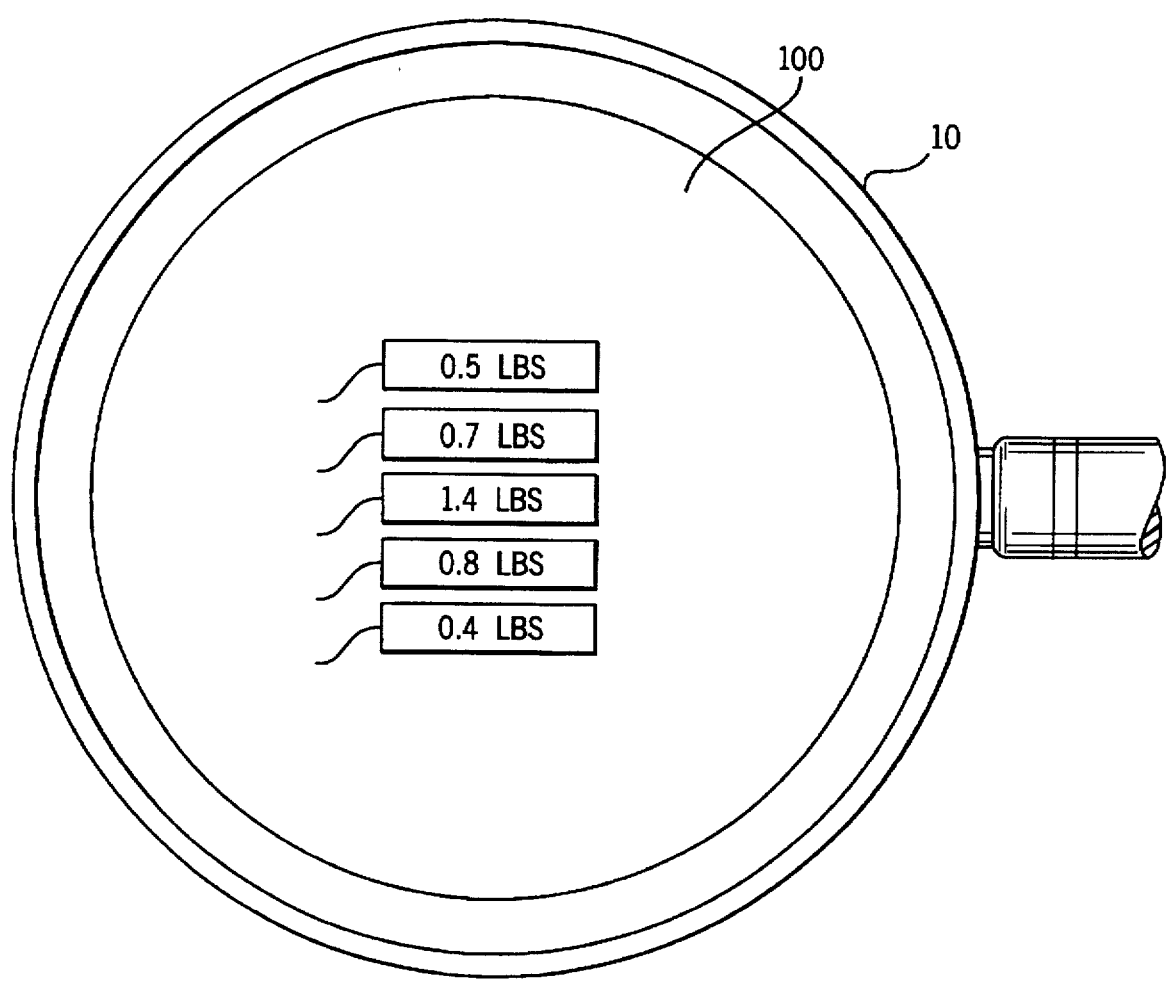

METHOD AND APPARATUS FOR FINISH SURFACE TESTING

BACKGROUND OF THE INVENTION

The present invention relates generally to the field of surface finish testing, and more particularly to a unique test procedure and apparatus for testing the surface finish applied to cooking vessels.

In the case of cooking vessels, it has been found to be desirable to apply a nonstick surface finish to the cooking surface of the vessel. A nonstick surface finish makes the vessel generally easier to clean and use. One problem with this type of nonstick surfaces is that they tend to be softer than other types of cooking vessels surfaces. As such, they are much more susceptible to scuffing and scratching that eventually causes the surface to wear or tear away, thereby revealing the bare material, usually metal, to which the nonstick finish was applied. Consequently, it is desirable to provide a testing procedure and accompanying testing apparatus that will accurately and precisely inform the manufacturer of cooking vessels and other objects with coated surfaces of surface durability to insure consistent application. This will consequently accurately inform and provide customers and the general public of the amount of scuffing or other abrasion that the cooking or other coated surface can safely sustain. Further, the present testing method and apparatus allows the manufacturer to accurately gauge the quality of the coated or finished surfaces in a more definitive manner.

More specifically, the present method and apparatus allows for testing the durability of a coated or finished surface wherein the test surface is scraped while hot (if desired) with sharp cutters which will not dull or change its cutting edge over the period of the test. This improved procedure contrasts with former procedures, such as that disclosed in my copending patent application Ser. No. 08/182,921, filed 14 Jan. 1994 directed to a method wherein a coated object is subjected to a rotating web of abrasive material while being moved in a cyclical pattern. Other known surface finish test procedures including the use of metallic scrubbing brushes, selected abrasive particulate matters, the bottom surface of a wooden spatula, pressure applied to a metal ball, perforated pressure plates, sponges containing a particulate abrasive material, all of which are either subject to wear or clogging During a given test period.

SUMMARY OF THE INVENTION

The invention comprises a method and apparatus for carrying out a surface finish durability test procedure. The preferred apparatus for carrying out the method of testing comprises a horizontally slideable fixture having its forward and reverse motion controlled by a prime mover as a gear motor driving an eccentric linkage attached to one end of the slideable fixture. The fixture alternatively slides towards and away from a stationary support arranged for securing and supporting a cooking vessel having a surface finish to be tested. A heater and heater temperature control is provided for heating the surface finish to a preselected test temperature. Mechanical surface testing is provided by at least one scraper having a sharp or keen edge arranged to scrape the surface responsive to the forward and reverse horizontal motion of the slideable fixture. Means are provided to alternatively respectively raise and lower the scraper with respect to the surface to be tested and responsive to forward and reverse motion of the fixture. Fine adjustment means are also provided to regulate selected pressure settings of the scraper edge with respect to the surface finish to be tested.

The method for determining the mechanical durability of the surface finish of a cooking vessel uses the aforesaid apparatus. The method is generally performed as follows: Securing a cooking vessel to the stationary support and heating the pan, while resting on the support, to a preselected temperature as required for testing a particular surface finish preapplied to the exposed surface of the cooking vessel. Presetting the required or desired test pressure exerted by the scraper keen edge against the test surface. For each of the areas to be scraped and after one or more scraping or abrading functions have been made, measure the thickness of the surface finish, and in particular recording the mean thickness, lowest reading, highest reading and standard deviation.

These and other benefits of the present invention will be apparent one skilled in the art from the following description.

DESCRIPTION OF THE DRAWINGS

FIG. 12 is a top plan view of a cooking vessel showing the surface finish and predetermined abraded areas to be tested and the pressure measured in pounds applied thereto.

DETAILED DESCRIPTION

Although the disclosure hereof is detailed and exact to enable those skilled in the art to practice the invention, the physical embodiments herein disclosed merely exemplify the invention which may be embodied in other specific structure. While the preferred embodiment has been described, the details may be changed without departing from the invention, which is defined by the claims.

Figure 1:
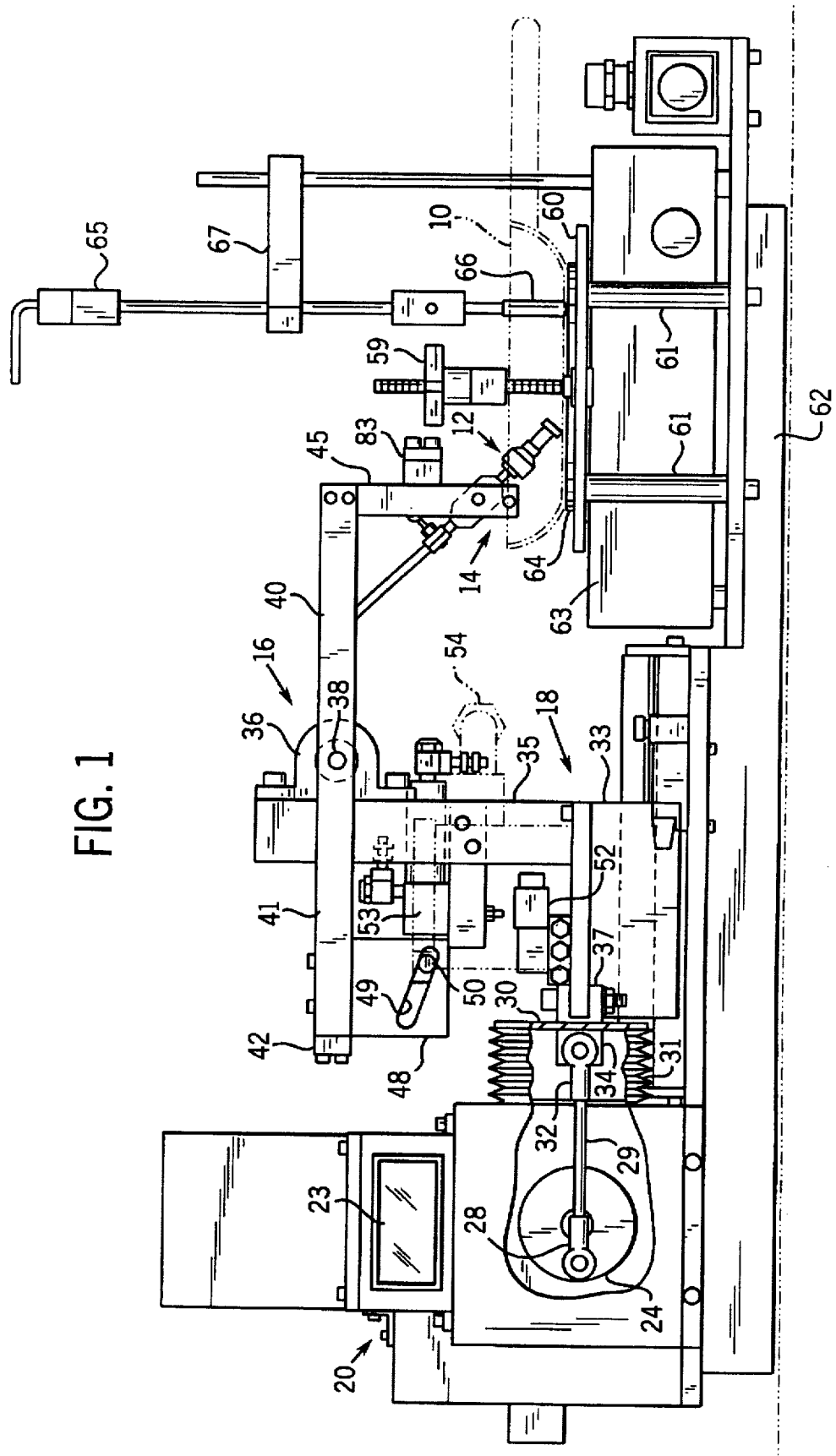
FIG. 1 is a side elevational view of the apparatus of this invention.
Figure 2:
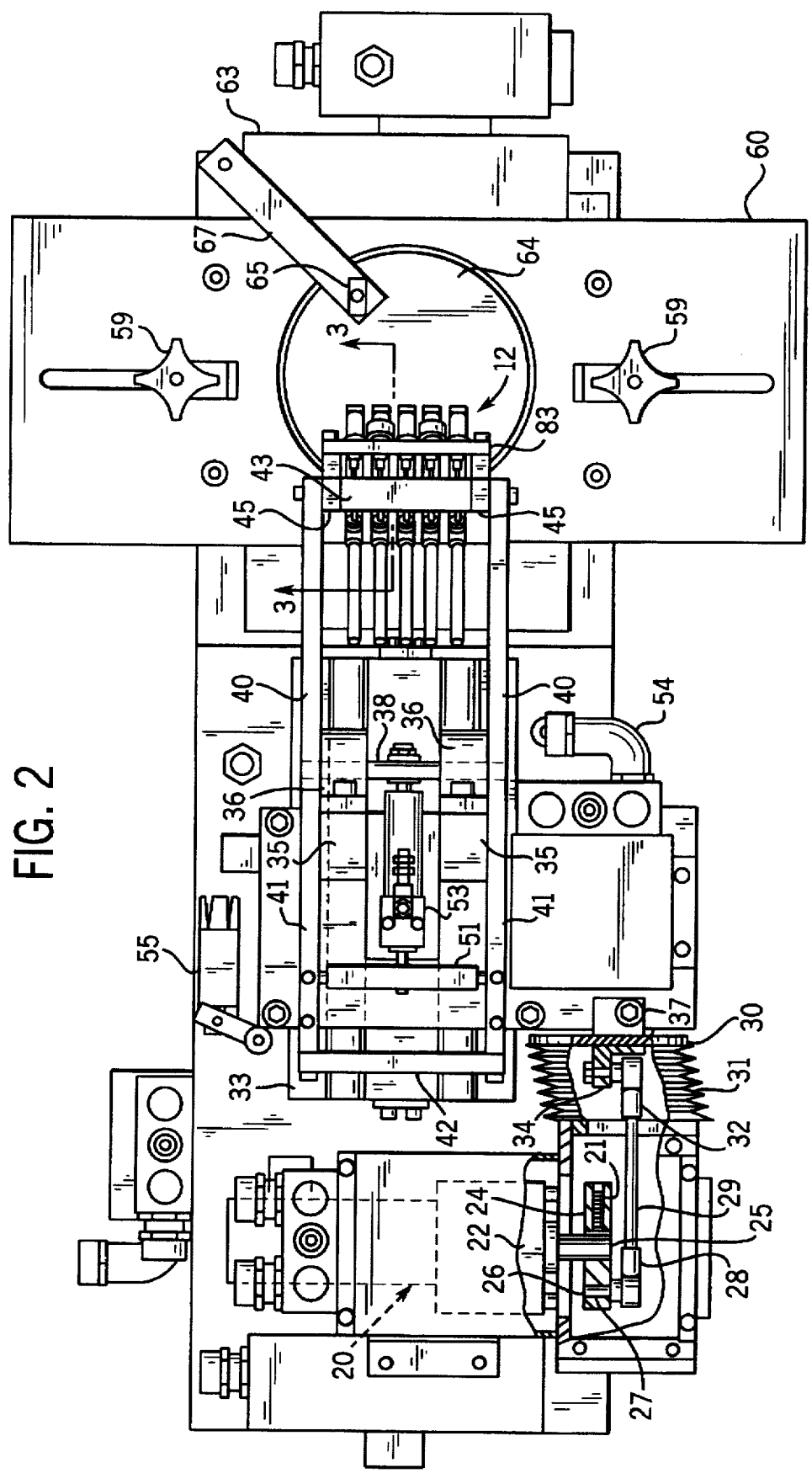
FIG. 2 is a top plan view of the apparatus of FIG. 1.

With reference to the drawings in general, and in particular to the views of FIGS. 1 and 2, the improved apparatus used for testing mechanical durability of a cooking vessel 10 comprises, in general, scraper mechanisms 12, a pivotable support 14 for the scraper mechanisms 12, oppositely disposed, first-class lever members 16 pivotally supported by a horizontally slidable supporting fixture 18 actuated by a prime mover 20. It will be observed that the prime mover 20 comprises an adjustable speed, conventional gearmotor 22 including a tachometer 23 for observing speed adjustment of the gearmotor 22. The gearmotor 22 provides an eccentric drive by rotating a wheel 24 keyed to the drive shaft 25 of the gearmotor 22 by means of a conventional Allenhead screw 21 (See FIG. 2). The wheel 24 includes an aperture 26 radially spaced from the drive shaft 25 of the gearmotor 22. The aperture 26 rotatably receives a stud 27 projecting from a knuckle 28 attached to a rod 29. The opposite end of the rod 29 pivotally engages a knuckle 32 pivotally joined to a trunnion 34. The trunion 34 projects inwardly from the endwall 30 of a transversely movable bellows 31. The bellows endwall 30 is provided, on its exterior surface, with a knuckle 37, pivotally attached to the base 33 of the horizontally slidable fixture 18. The fixture is commercially available, and known as a Thompson Slide. The respective pivot attachments between the prime mover 20, its drive shaft 25, the radially extending aperture 26 of the wheel 24, its rotatable stud 27, the eccentrically movable rod 29, pivotally attached to the trunnion 34 and the bellows endwall 31, translate into an eccentrically driven, alternative forward and reverse, horizontal linear movement of the slidable fixture 18.

The fixture 18 includes a standard, or upright member 35, having spaced, apertured trunions 36 supporting a pivot pin 38 for pivotally supporting the first-class lever 16. Each of the oppositely disposed lever members 16 include oppositely extending lever arms 40 and 41. The lever arms 41 are connected for simultaneous movement by means of a supporting crossbar 42, whereas the arms 40 are joined for simultaneous movement by means of a crossbar 43. Projecting below the crossbar 43, the distal ends of each of the lever arms 40 include bearing supports 45 for supporting the scraper mechanisms 12, as will hereinafter be described.

The lever arms 41 support at their distal end portions a pair of depending slotted plates 48. Each plate 48 defines registering angularly disposed cam slots 49, supports a cam follower 51 by means slidably receiving axially extending pins 50 engaging the slots 49, to provide a camming mechanism for alternatively raising and lowering the scraper mechanisms 12 supported by the crossbar 43 and bearing supports 45 depending from, the distal ends of the lever arms 40.

A solenoid 52 actuates the cam follower 51 by means of operating the adjustable, conventional Bimba Cylinder mechanism 53. The camming movement causes the scraper mechanisms 12 to be alternatively raised upwardly and downwardly depending upon actuation of the solenoid 53. Rearward and forward movement of the slidable supporting fixture 18 is controlled by the limit switches 54 and 55, respectively. Vessel heating means are provided to be used for certain preselected testing procedures. As stated previously, the cooking vessel 10 is preferably secured to a supporting plate 60, which in turn, is supported by columns or standards 61. The columns 61 are secured to a base member 62. Mounted below the base 60 is a heating unit 63. The heating unit 63 is controlled by means of a temperature probe 65 supporting a thermocouple 66 having its distal end preferably touching the test surface 64 of the cooking vessel 10. The supporting probe holder 67 permits slidable height adjustment of the probe 65 and its thermocouple 66.

Figure 3:
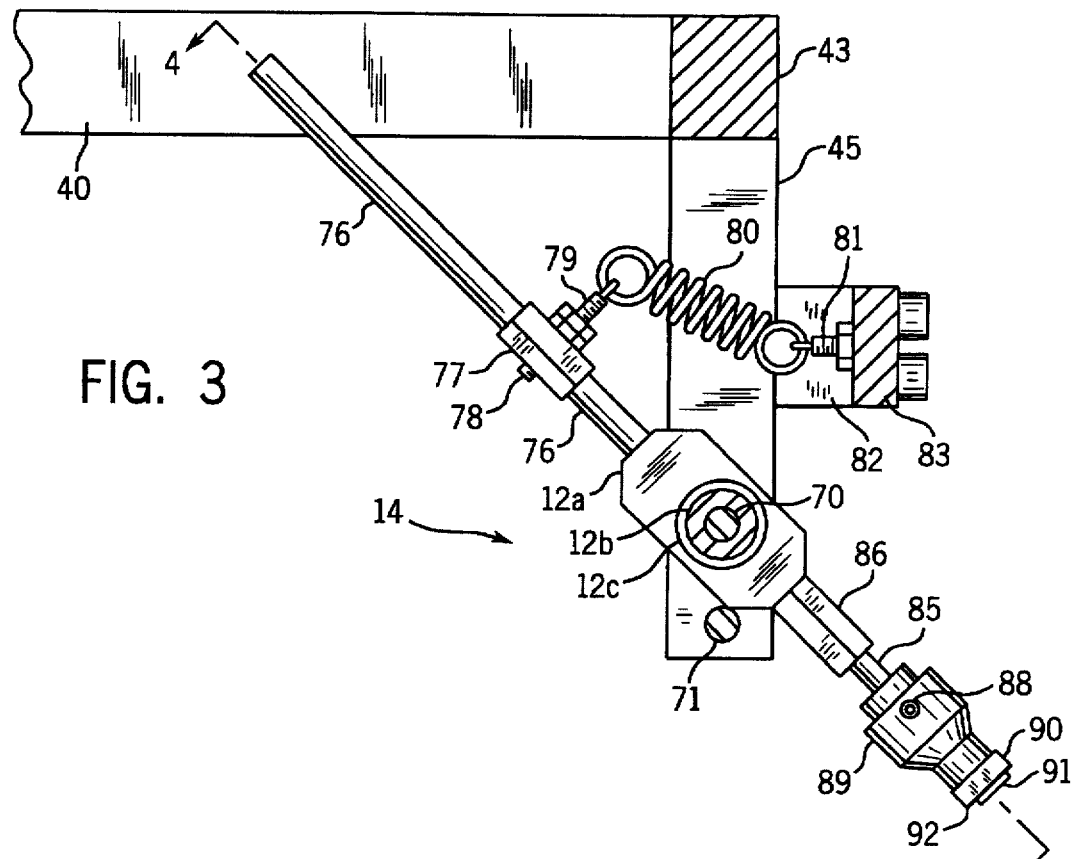
FIG. 3 is a fragmentary side view, partially in section, of a pivotally operated scraping mechanism, taken along lines 3—3 of FIG. 2 and showing mechanism in starting position.
Figure 5:
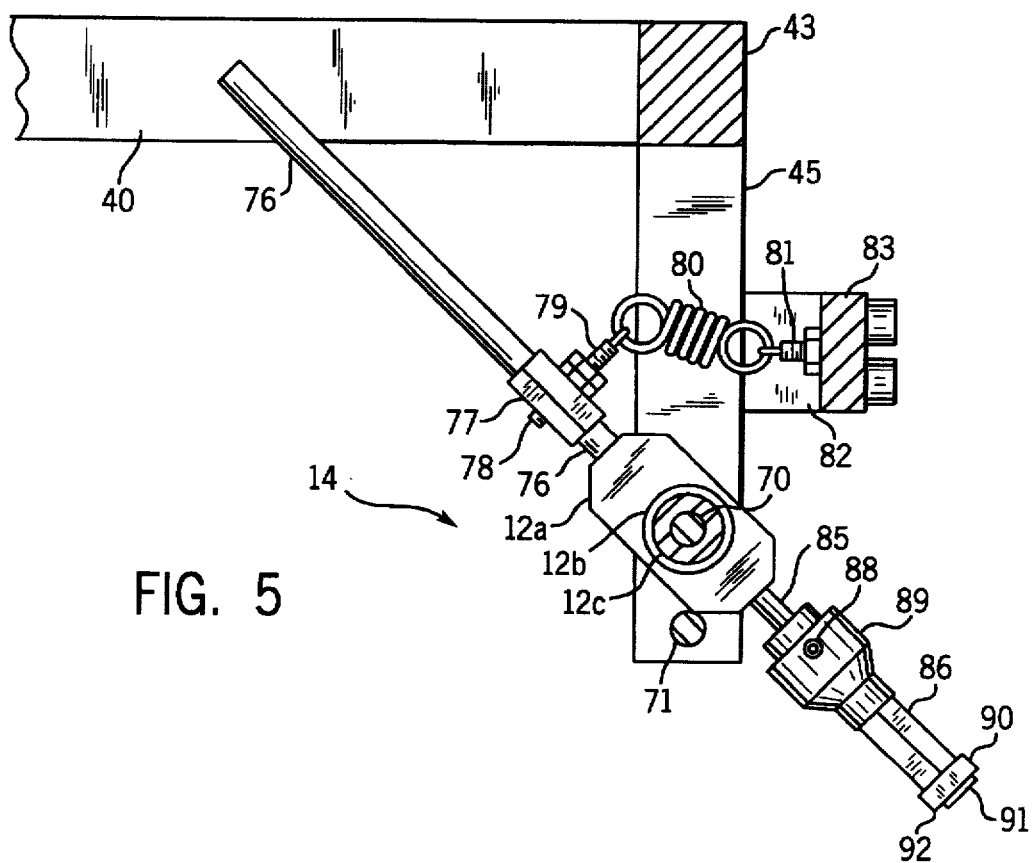
FIG. 5 is a fragmentary side view, partially in section, of the pivotally operated scraping mechanism of FIG. 3, and showing the mechanism in scraping position.
Figure 4:
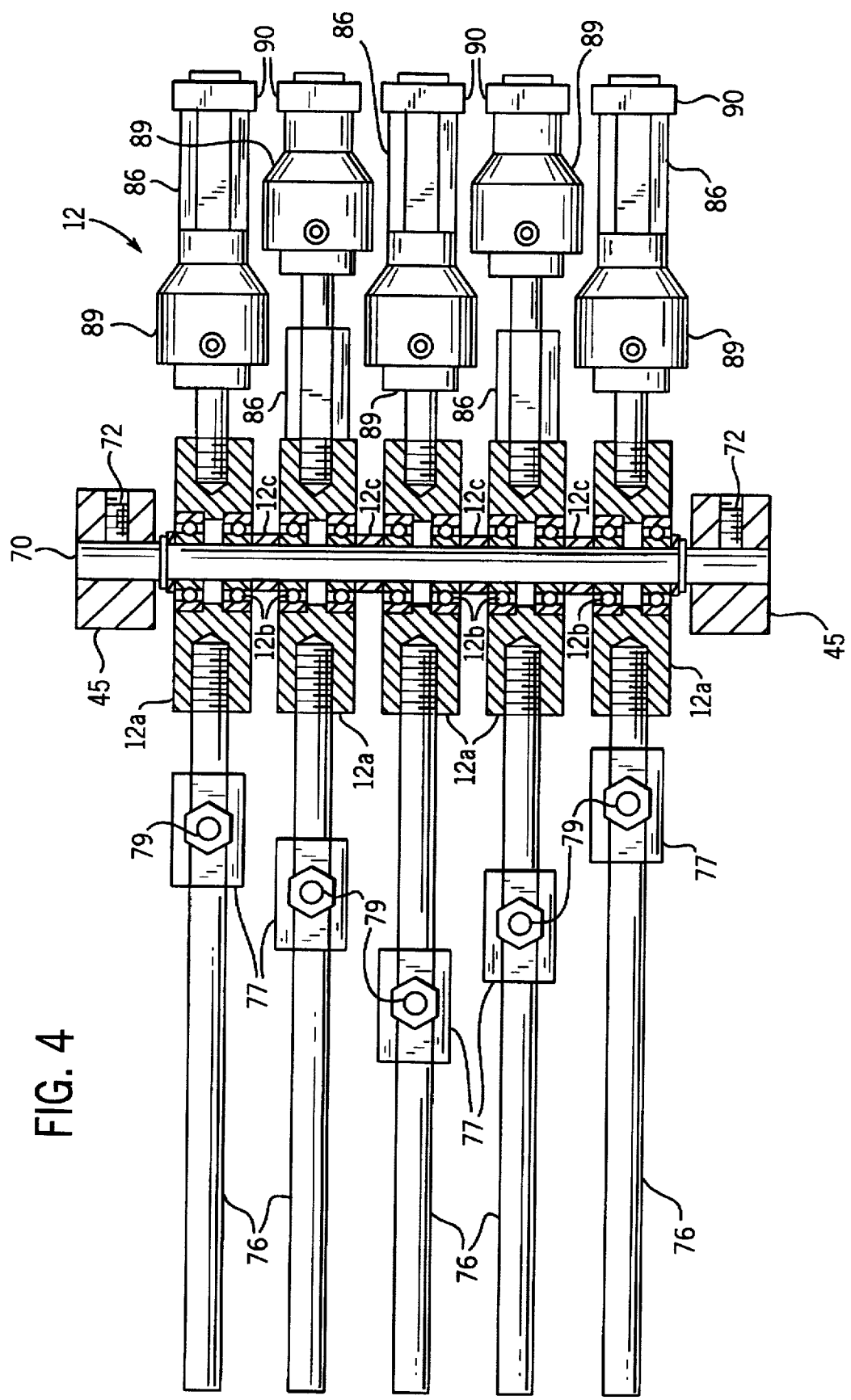
FIG. 4 is a sectional view taken along lines 4—4 of FIG. 3, and detailing the scraper mechanisms of this invention.

Referring next to the views of FIGS. 3, 4 and 5, the scraper mechanisms 12 are supported between oppositely disposed bearing supports 45 depending from the lever arms 40. The mechanisms 12 are each further supported by a pivot shaft 70 suspended between the oppositely disposed bearing supports 45, and being secured thereto by means of set screws 72. Individual scraper support members 12a contain ball bearings 12b, the scraper support members 12a are axially spaced from one another by means of spacers 12c. An elongated adjusting rod 76 extends upwardly from each support member 12a and is arranged to slidably receive a coupling member 77 secured to a preselected operating position on the rod 76 by means of set screws 78. A spring anchor 79 projects from the coupling member 77 to anchor one end of a helical extension spring 80. The spring 80 is anchored at its opposite end to an anchor pin 81 projecting from a stationary spring support 82 fastened to the opposed bearing supports 45 and having an anchor bar 83 joined with each of the supports 45.

Extending downwardly from each of the scraper support members 12a are the individual scraper devices comprising the aforementioned scraper mechanisms. The devices each include threaded studs 85 arranged for threading engagement with threaded apertures in respective support members 12a. Alternate studs 85 project from spacers 86, which arrangement provides a means of minimizing the space between the supports 45, and to provide room for additional scraping mechanisms 12, when desired. A maximum number of five mechanisms 12 fitting the present commercial Thompson Slide are shown for illustrative purposes only. The mechanisms 12 each include a mounting member 89 secured to a respective stud 85 by means of set screws 88. Each mounting member 89 is arranged at its lower end to receive conventional Kennametal Inserts 90 held thereto by means of cap screws 91. The Inserts 90 have at least one sharpened or keen edge 92 arranged for scraping engagement with the cooking vessel 10 surface finish 100 to be tested.

Operation

The various stages of accomplishing the procedure and operation of the apparatus of this invention is best described with reference to the views of FIGS. 6–12, inclusive. In the present procedure the improved apparatus and method were used to test a non-stick surface finish or coating 100, such as TEFLON®, applied to a thermally sprayed metallic surface of either stainless steel or aluminum, or any other suitable supporting vessel surface.

Figure 6:
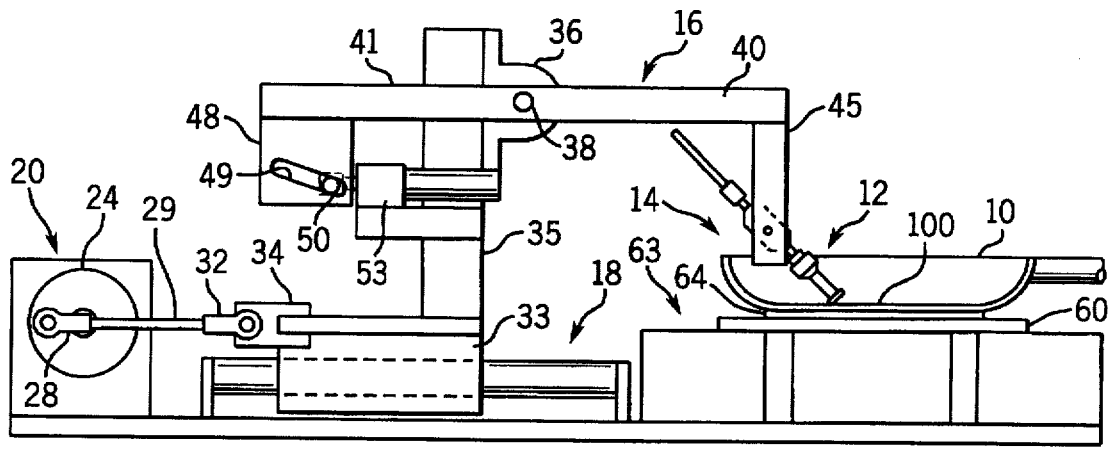
FIGS. 6–8, inclusive, are a series of side view elevational sketches illustrating the relationship of cooperating elements of the improved apparatus as the scraping mechanisms are moved to accomplish the method steps of this invention.

The view of FIG. 6 shows the improved apparatus in the start position with the cam follower pin 50 in the lower end of the angular camming slot 49, and with the levers 16 is substantial horizontal position. The mechanisms 12 are shown resting on the finish surface 100 of the test vessel or pan 10. Prior to startup the valves (not shown) controlling the Bimba Cylinder 53 are adjusted to establish the initial test pressure exerted by the respective Kennametal Inserts 90. The Inserts 90 are not allowed to hit the pan surface 100 hard enough to cause excessive wearing of the keen edge 92 of the respective insert 90. The valves are further adjusted to quickly pull off the Inserts 90 after the scratch stroke, to be later discussed. Preselected test pressure applied by the individual Kennametal Inserts 90 is adjusted by moving the respective coupling members 77 up or down the rod 76 after releasing the set screws 78. The initial pressure is accurately measured by means of a conventional push-pull gauge (not shown) by individually pulling the mechanisms 12 upwardly and adjusting from there. Readings are taken when the respective Insert 90 just barely leaves the surface of the pan 10. In the preferred embodiment described herein, the pressures to set the Inserts are 0.5 lb., 0.7 lb., 1.4 lb., 0.8 lb. and 0.4 lb., respectively, in the five test positions illustrated in the view of FIG. 12. The scratch tools (Kennametal Inserts 90) are preferably K9 carbide with a 90° edge of Rockwell "A" scale hardness of 89.5. The Inserts 90 scratch the surface at a 45° angle and provide a 2 inch scratch every second and one complete cycle every two seconds. The established testing procedure requires the scraper action to continue for one hour.

As mentioned above, the Kennametal Inserts 90 are preferably square-shaped to permit rotation of 90 degrees after each test to ensure even use of the sharp edges.

Most test procedures require the pan or vessel 10 to be preheated. For example, in the present illustration, and for the test pressures set forth above, the preselected temperature test temperature is set at 400 degrees Fahrenheit. Heat is supplied by the heat unit 63, measured by the thermocouple 66, which transfers the temperature reading to a thermostat (not shown) controlling the heater unit 63.

Figure 7:
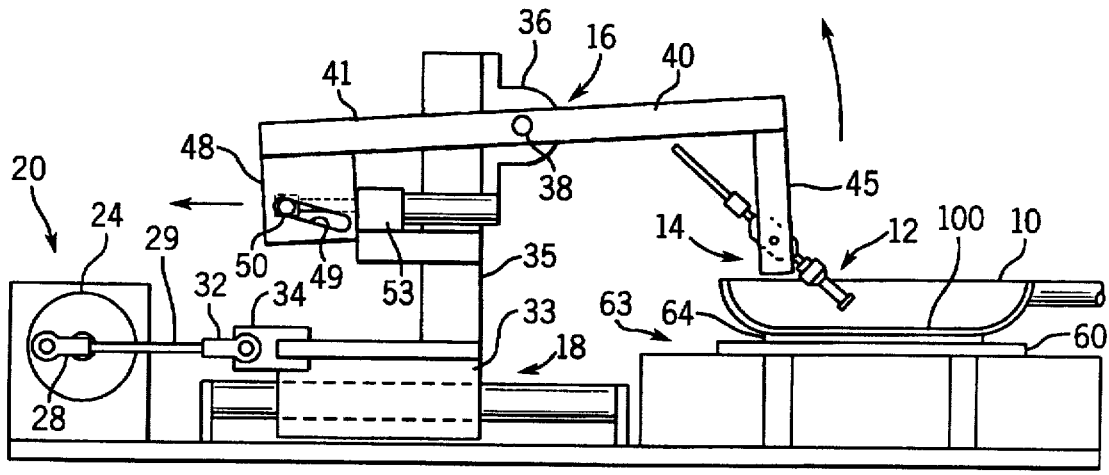
Figure 8:
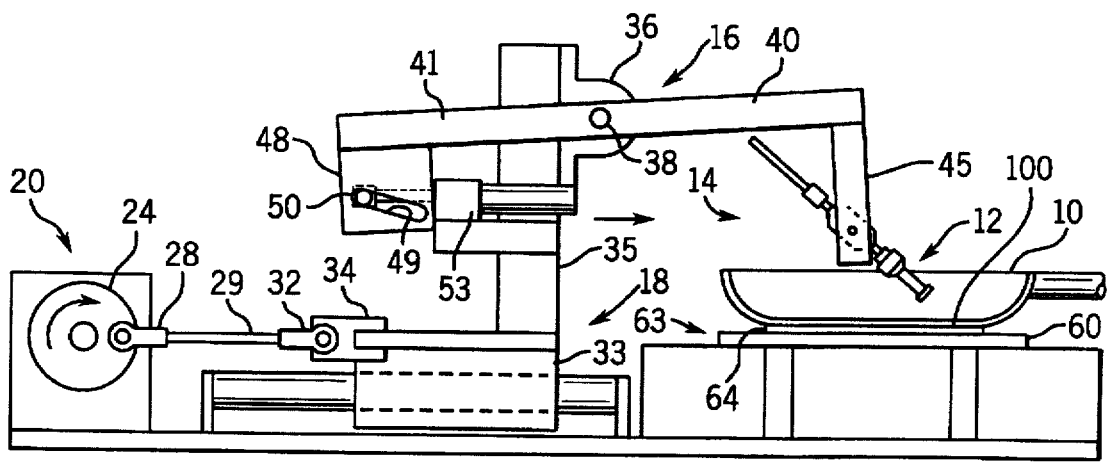

Referring next to the view of FIG. 7, it will be noted that the Thompson Slide 18 remains in the same position as shown in FIG. 6, i.e., with the eccentric knuckle 28 moving the base 33 to a position farthest to the left. However, the Bimba Cylinder 53 is operated the solenoid 52 to force the cam follower pins 33 to ride in their slots 49 and lift the lever 16 counterclockwise about the pivot 38 to thereby cause the bearing supports 45 to rise. As the supports 45 rise, they take with them the scraper mechanisms 12 in readiness for the forward move of the Slide 18. With the mechanisms 12 being held above the surface 100, the eccentric knuckle 28 is rotated by the gear motor 20 to the forward position shown in the view of FIG. 8.

Figure 9:
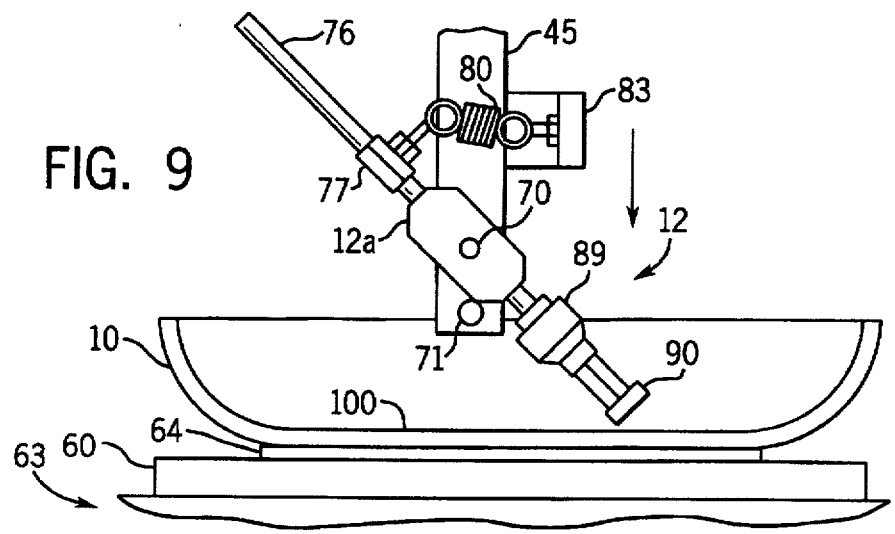
FIGS. 9–11, inclusive, are side elevational views of a cooking vessel with a nonstick surface finish applied thereto, and illustrating three positions of scraper mechanisms operating to test the durability and thickness of the finished surface.
Figure 10:
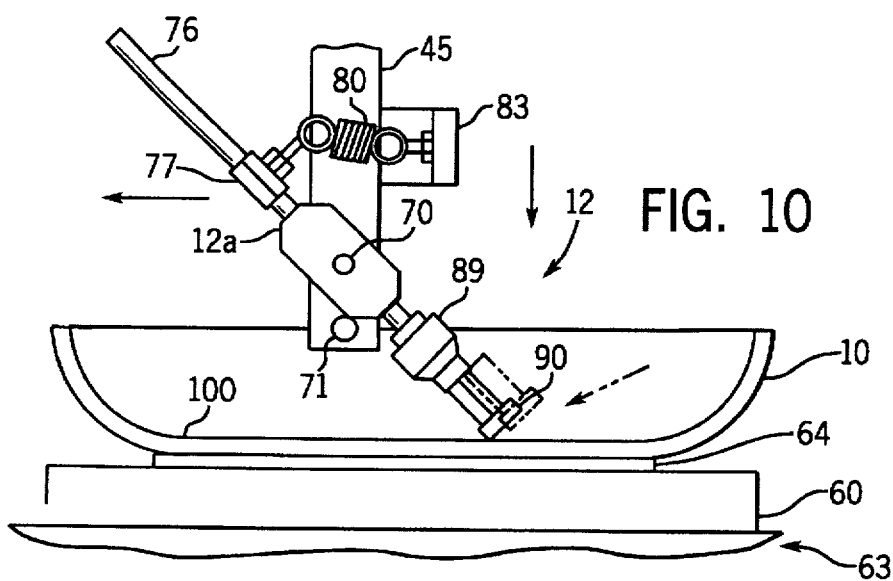
Figure 11:
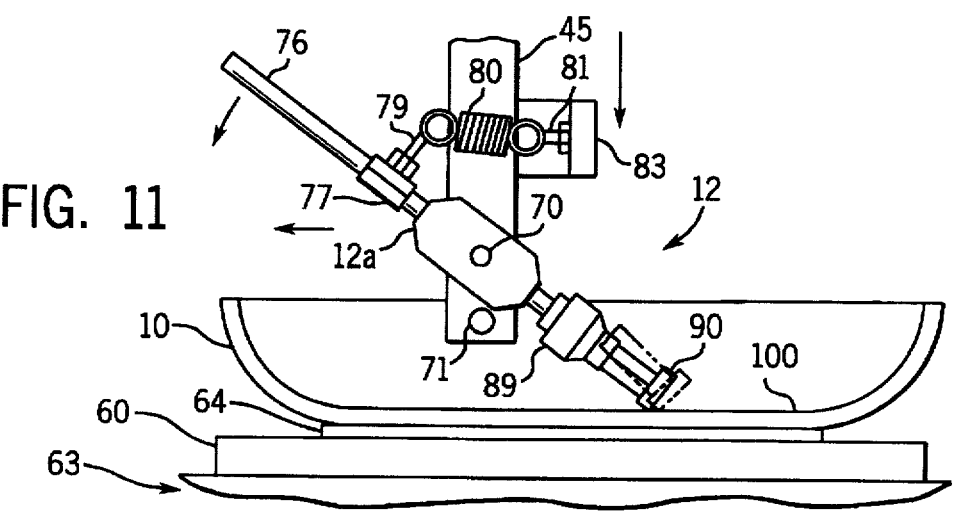

With reference to FIG. 9, this enlarged view illustrates the position of the scraper mechanism 12 with its scraper Insert 90 held just above the surface 100. FIG. 10 shows the Kennametal Insert 90 being moved downwardly upon clockwise rotation of the lever 16 and with the Insert 90 being readied for scraping action upon return of the Thompson Slide mechanism 18 being returned to its start position of FIG. 6. The solenoid 52 is timed to cause the clockwise action, and the mechanisms 12 are held in the FIG. 11 position by action of the respective coil springs 80 at the respective pressures and paths exhibited in FIG. 12. The scraping cycle illustrated in the progressive views of FIGS. 6-11, inclusive are cycle for one hour for the particular established test procedure.

The test procedures recommended include an initial measurement of the surface thickness 100 by means of a Fischerscope Magna, Eddy, Multi 750 of the type sold by Fischer Technology, Inc. of 750 Marshall P{helps Road, Windsor, Conn. 06095-2199. This measuring device is preferred, although any other suitable method may also be used, e.g. a micrometer. The surface is again measured upon completion of the established number of scraping cycles by measuring in three places along the 2 inch length of the abrasion. The mean thickness, lowest reading, highest reading and standard deviation are recorded.

The above described embodiment of this invention is merely descriptive of its principles and is not to be limited. The scope of this invention instead shall be determined from the scope of the following claims, including their equivalents.

What is claimed is:

1. An apparatus for determining the mechanical durability of a test surface finish of an object, said apparatus comprising; means for supporting said object; a surface scraper support fixture in horizontally movable relationship with said object support means, and comprising, lever support means including a pivot support element, a lever defining a pair of oppositely disposed end portions, and being pivotally supported intermediate its end portions by said pivot support element, inclined cam means located proximate a first end portion for alternatively raising and lowering the opposed end portions of the lever, at least one surface scraper including an element defining at least one keen edge transversely engageable with said test surface finish and arranged to traverse and scrape a preselected test length of said surface finish, secondary pivot means located proximate the second lever end portion and depending therefrom to pivotally support said scraper, said scraper including bearing support means pivotally engaging said secondary pivot means, pressure adjustment means for finely adjusting the contact pressure applied to the keen edge of said pivotally supported scraper with respect to the surface to be tested, and primemover means arranged to provide alternative horizontal movement between said support fixture and said object support means.

2. The apparatus of claim 1, wherein the object is a cooking vessel.

3. The apparatus of claim 1 including means for heating the test surface finish of said object, and including temperature control means for selecting and establishing a desired test temperature for said heating means.

4. The apparatus of claim 1, wherein the means for alternatively raising and lowering the opposite end of the lever comprises an inclined cam surface located proximate to the said one end portion of said lever, and a cam follower extending laterally from said support surface and slidably engageable with said inclined cam surface.

5. The apparatus of claim 1, wherein a pair of levers are provided and are laterally spaced from one another and each respectively comprises a pair of lever members, wherein said secondary pivot means comprises a common pivot member extending between and supported by the second lever portions of the respective lever members, and wherein a plurality of surface scrapers and their individual bearing support means are pivotally supported by said common pivot member and are positioned adjacent one another, and wherein spacer means are provided to permit individual pivoting of respective surface scrapers.

6. The apparatus of claim 1, wherein the pressure adjustment means comprises a rod extending from said scraper support bearing oppositely from said scraper, a coupling member arranged for sliding movement on said rod, set screw means for positioning and securing said coupling member on said rod, and spring biasing means for interposed between said coupling member and said depending secondary pivot means.

7. The apparatus of 6, wherein a the pressure adjustment means comprises a series of individual rods extending respectively from individual scraper support bearings, individual coupling members positioned on each rod, set screw means for securing the respective coupling members to its rod, and individual spring biasing means for respective each coupling member.

8. The apparatus of claim 1, wherein the primemover comprises a gearmotor, means for controlling the speed of said gearmotor, a drive wheel driven by said gearmotor, and an eccentric drive mechanism positioned between said drive wheel and horizontally movable scraper support fixture for alternative movement thereof.

\* \* \* \* \*